United States Patent [19]

Butler et al.

[11] Patent Number: 4,956,511
[45] Date of Patent: Sep. 11, 1990

[54] TOLUENE DISPROPORTIONATION PROCESS

[75] Inventors: James R. Butler, Houston; J. Randall Curtis, Webster, both of Tex.

[73] Assignee: Fina Technology, Inc., Dallas, Tex.

[21] Appl. No.: 293,374

[22] Filed: Jan. 4, 1989

[51] Int. Cl.$^5$ .............................................. C10C 3/62
[52] U.S. Cl. .................................... 585/475; 585/470; 585/474
[58] Field of Search .......................................... 585/475

[56] References Cited

U.S. PATENT DOCUMENTS

| | | | |
|---|---|---|---|
| 3,436,174 | 4/1969 | Sand | 23/113 |
| 3,476,821 | 11/1969 | Brandenburg et al. | 260/672 |
| 3,480,539 | 11/1969 | Voorhies et al. | 208/111 |
| 3,506,731 | 4/1970 | Frilette et al. | 585/475 |
| 3,527,826 | 9/1970 | Sonoda et al. | 585/475 |
| 3,562,345 | 2/1971 | Mitsche | 260/672 |
| 3,677,973 | 7/1972 | Mitsche et al. | 252/455 Z |
| 3,721,717 | 3/1973 | Suld et al. | 585/475 |
| 3,792,098 | 2/1974 | Brandenburg | 585/475 |
| 3,808,284 | 4/1974 | Wallace et al. | 585/475 |
| 4,011,276 | 3/1977 | Chu | 585/475 |
| 4,016,219 | 4/1977 | Kaeding | 585/475 |
| 4,038,335 | 7/1977 | Minachev et al. | 585/475 |
| 4,052,476 | 10/1977 | Morroson | 585/475 |
| 4,151,120 | 4/1979 | Marcilly | 252/455 Z |
| 4,665,258 | 5/1987 | Butler et al. | 585/475 |
| 4,723,048 | 2/1988 | Dufresne et al. | 585/475 |
| 4,723,049 | 2/1988 | Menard et al. | 585/475 |
| 4,761,514 | 8/1988 | Menard | 585/475 |

FOREIGN PATENT DOCUMENTS

| | | | |
|---|---|---|---|
| 746087 | 2/1969 | Belgium | 585/475 |
| 1019353 | 10/1971 | Canada | 585/475 |
| 1207903 | 4/1986 | U.S.S.R. | 585/475 |

OTHER PUBLICATIONS

Kirk-Othmer, Encyclopedia of Chemical Technology, 3rd Edition, 1981, "Molecular Sieves", vol. 15, pp. 638-643.

Bhavikatti et al., "Toluene Disproportionation Over Aluminum-Deficient and Metal-Loaded Mordenites. 1. Catalytic Activity and Aging", Ind. Eng. Chem. Prod. Res. Dev. 1981, 20, pp. 102-105, Aug.

Primary Examiner—Helane Myers
Attorney, Agent, or Firm—John K. Abokhair; William D. Jackson; Jimmy D. Wheelington

[57] ABSTRACT

Process for the disproportionation of toluene over a nickel modified mordenite catalyst in which catalyst activity and aging quality are enhanced for carrying out the disproportionation reaction under relatively low temperature conditions with small increases of temperature as the process continues. The catalyst is loaded into a catalytic reaction zone. A preflush gas such as hydrogen is passed into the reaction zone while withdrawing the gas from the reaction zone and progressively increasing the temperature of the reaction zone to a desired level. A toluene feedstock is then passed into the reaction zone. Hydrogen is supplied with the toluene to the reaction zone, normally at a hydrogen/toluene mole ratio of 4 or less. At the conclusion of the initial transient conditions accompanying the initiation of toluene feed to the reaction zone, initial steady state conditions for disproportionation of toluene to benzene and xylene in the presence of the catalyst are established. The initial toluene conversion rate is at least 40% with an initial steady state reactor temperature (as measured at the reactor inlet) within the range of 600°-800° F., and a temperature gradient across the reactor of no more than 50° F. The process is continued at a toluene conversion rate of at least 40% while retaining the activity of the catalyst, as indicated by toluene conversion, at an average progressive incremental temperature increase of no more than 7° F. per week, as normalized by changes in space velocity of the toluene feedstock over the catalyst bed.

30 Claims, 8 Drawing Sheets

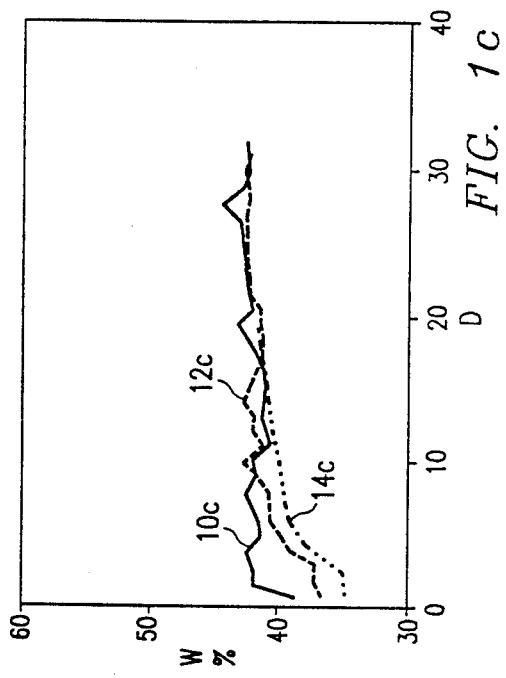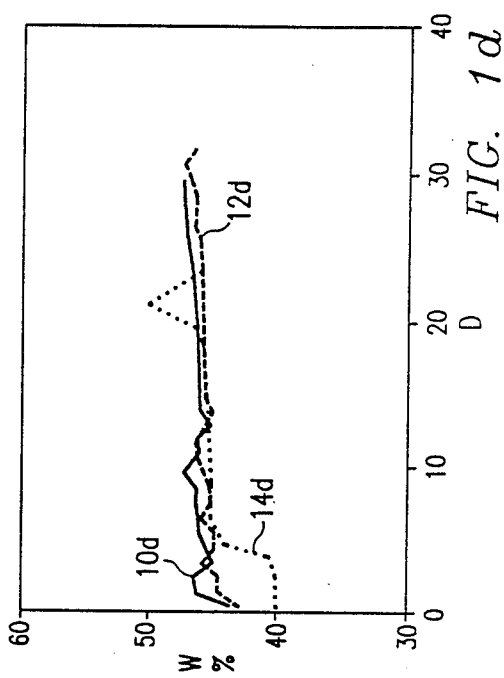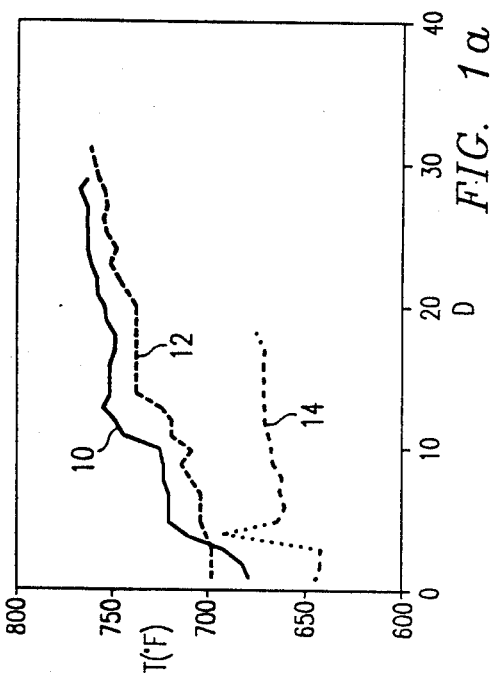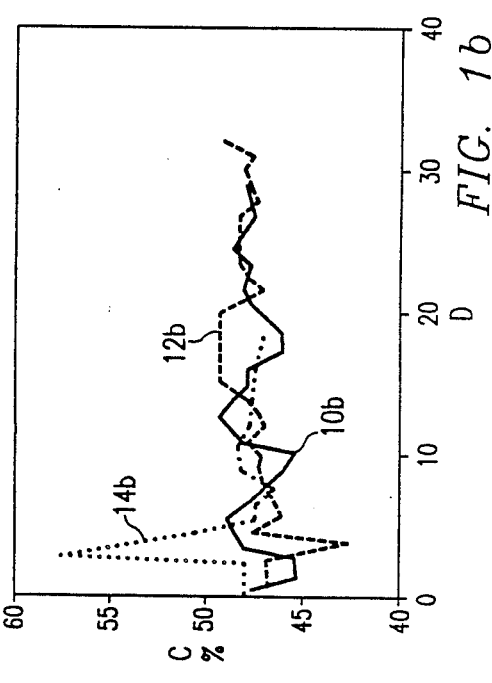

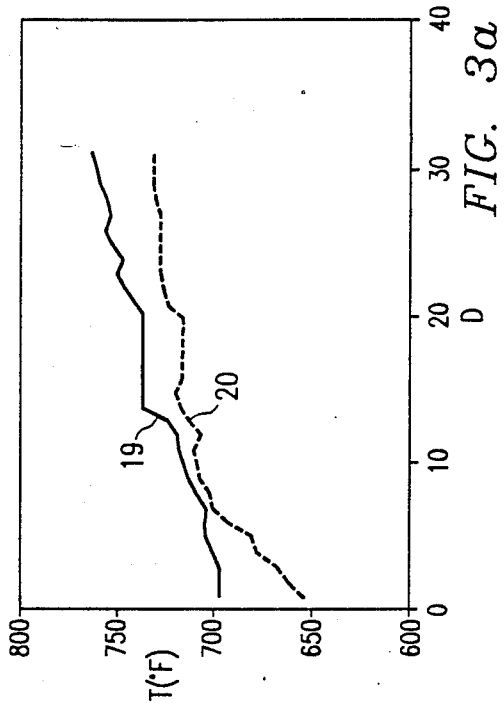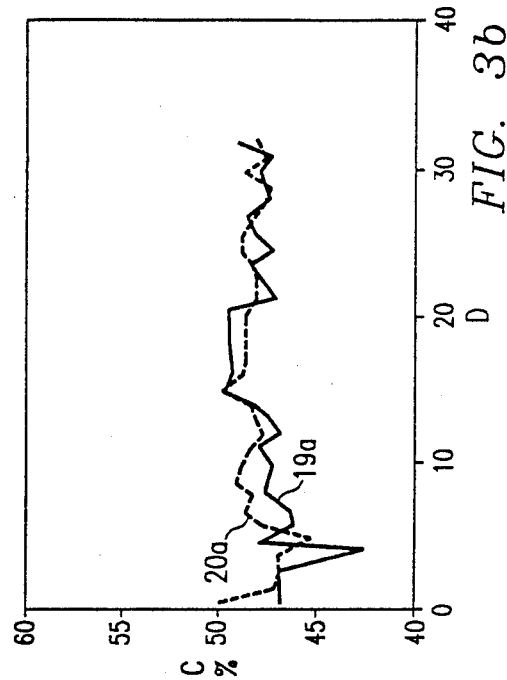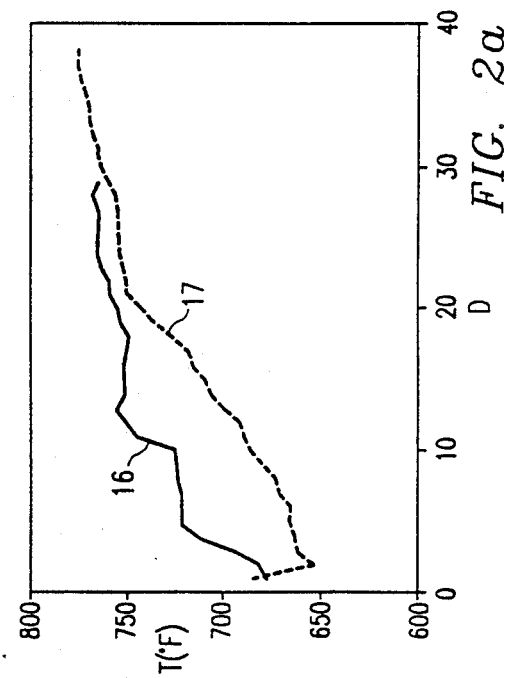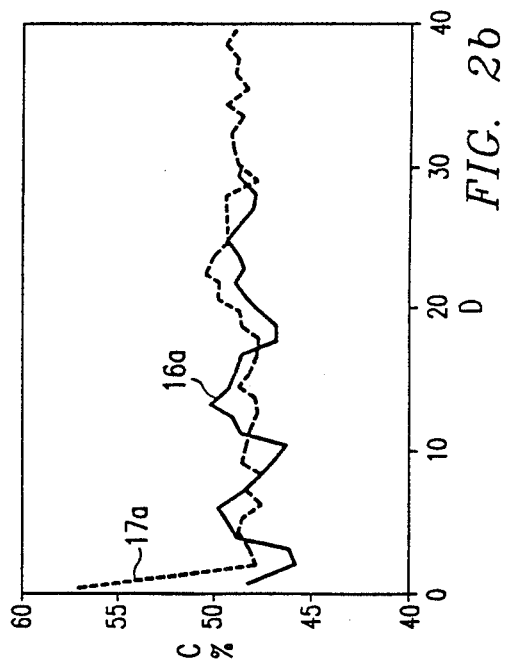

TOLUENE DISPROPORTIONATION PROCESS

ART BACKGROUND

The disproportionation of toluene involves a well known transalkylation reaction in which toluene is converted to benzene and xylene in accordance with the following reaction:

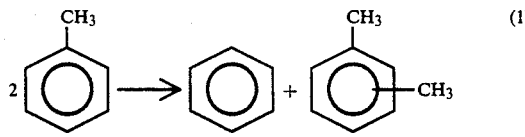

Reaction (1) is mildly exothermic.

Mordenite is one of a number of molecular sieve catalysts useful in the transalkylation of alkylaromatic compounds. Mordenite is a crystalline aluminosilicate zeolite having a network of silicon and aluminum atoms interlinked in this crystalline structure through oxygen atoms. For a general description of mordenite catalysts, reference is made to Kirk-Othmer, *Encyclopedia of Chemical Technology*, 3rd Edition, 1981, under the heading "Molecular Sieves", Vol. 15, pages 638–643. Mordenite, as found in nature or as synthesized to replicate the natural zeolite, typically has a relatively low silica to alumina mole ration of about 10 or less. However, mordenite catalysts having substantially lower alumina contents are also known. These aluminum deficient mordenite catalysts have silica/alumina ratios greater than 10, ranging up to about 100, and may be prepared by direct synthesis as disclosed, for example, in U.S. Pat. No. 3,436,174 to Sand or by acid extraction of a more conventionally prepared mordenite as disclosed in U.S. Pat. No. 3,480,539 to Voorhies et al. Both the normal and the aluminum deficient mordenites are known to be useful in the disproportionation of toluene.

The disproportionation of toluene feedstocks may be carried out at temperatures ranging from about 200° C. to about 600° C. or above and at pressures ranging from atmospheric to perhaps 100 atmospheres or above. However, the catalyst itself may impose constraints on the reaction temperatures in terms of catalyst activity and aging characteristics. In general, the prior art suggests the use of relatively high temperatures when employing the high aluminum mordenites (low silica to alumina ratios) and somewhat lower temperatures when employing the low alumina mordenites. Thus, where mordenite catalysts having high silica/alumina ratios have been employed in the transalkylation of alkylaromatics, it has been the practice to operate toward the lower end of the temperature range. However, U.S. Pat. No. 4,665,258 to Butler et al. discloses disproportionation of a toluene containing feedstock employing an aluminum deficient mordenite catalyst under relatively severe disproportionation conditions; involving a temperature range of 370°–500° C. The mordenite catalysts have silica/alumina mole ratios of at least 30 and, more desirably, within the range of 40–60. The feedstock may be supplied to the reaction zone containing the mordenite catalyst at rates providing relatively high space velocities. The toluene weight hourly space velocity (WHSV) may be greater than 1. Hydrogen is supplied to the reaction zone at a hydrogen/toluene mole ratio within the range of 3–6. The hydrogen pressure may be 500 psi or more. The toluene feedstock need not be dried before supplying it to the reaction zone and the patent discloses toluene feedstocks having water contents in excess of 100 ppm.

Butler et al. also discloses passing a hot preflush gas, nitrogen or hydrogen, to the reaction zone prior to initiating the disproportionation reaction. The preflush gas is heated to a temperature sufficient to strip water from the catalyst so that it is substantially dehydrated by the time the toluene feed is started. This enables the disproportionation process to be carried out initially at a somewhat lower temperature without a reduced toluene conversion than would otherwise be the case. As the disproportionation process continues, the temperatures progressively increase to maintain the toluene conversion at the desired level, typically about 80% of theoretical.

U.S. Pat. No. 4,723,049 to Menard et al. discloses toluene disproportionation carried out over aluminum deficient mordenite of the type disclosed in the aforementioned patent to Butler. In this process, preferably carried out at a reaction zone temperature of 370°–500° C., and more preferably at a temperature of 400°–500° C. with an unpromoted aluminum deficient mordenite catalyst, the supply of toluene to the reaction zone is interrupted while the supply of hydrogen is continued. Preferably the period of interruption during which hydrogen supply is continued is for a period of at least one day before reinstating supply of the hydrogen feedstock to the reaction zone. This mode of operation is disclosed to enhance the aging quality of the catalyst and show a reduction in reactor zone temperature without a corresponding decrease in toluene conversion.

It is also a common practice to promote an aluminum deficient mordenite catalyst with a catalytically active metallic content. For example, U.S. Pat. No. 3,476,821 to Brandenburg et al. discloses disproportionation reactions employing mordenite catalysts having silica/alumina ratios within the range of 10–100 and preferably within the range of about 20–60. The mordenites are modified by the inclusion of a sulfided metal selected from the Group VIII metals. The metal may be included in the mordenite by well known ion exchange or impregnation techniques. The especially preferred sulfided Group VIII metals are cobalt and nickel present in a concentration of 0.5–10 weight percent. When compared with nickel oxide, nickel sulfide is said to provide less overactivity as indicated by gas and saturated hydrogencarbon yield. Here the desired temperature ranges are said to be from about 400°–750° F. and preferably 450°–640° F. The metal promoters are said to substantially increase activity and catalyst life, as indicated by runs extending over several hours or days.

As noted previously, hydrogen is supplied along with toluene to the reaction zone. While the disproportionation reaction (1) does not involve chemical consumption of hydrogen, the use of a hydrogen co-feed is generally considered to prolong the useful life of the catalyst, as disclosed, for example, in the above mentioned patent to Brandenburg. The amount of hydrogen supplied, which normally is measured in terms of the hydrogen/toluene mole ratio, is generally shown in the prior art to increase as temperature increases.

Bhavikatti et al., "Toluene Disproportionation Over Aluminum-Deficient and Metal-Loaded Mordenites. 1. Catalytic Activity and Aging", Ind. Eng. Chem. Prod. Res. Dev. 1981, 20, 102–105, discloses toluene disproportionation at 400° C. over mordenite catalysts having silica/alumina mole ratios ranging from 12 to 61 at atmospheric pressure and a space velocity (WSHV) of 1. As the silica/alumina mole ratio is increased, catalyst activity is substantially decreased while aging quality is increased. That is, the aging rates were lower. Based upon short term aging studies, the best silica/alumina mole ratio appeared to be 23. Catalyst decay was also suppressed by loading the mordenites with nickel. Mordenites having a silica/alumina ratio of 12, 16 and 23 were modified by the inclusion of nickel by a procedure involving ion exchanging ammonium mordenite with an aqueous solution of nickel nitrate. After ion exchange, the catalyst was activated under a hydrogen environment for two hours. The best activation temperature for nickel modified mordenite having a silica/alumina ratio of 23 was indicated to be about 550° C. The nickel modified mordenite having a silica/alumina ratio of 12 showed significantly lower activity when compared to the nickel loaded mordenite of a silica/alumina ratio of 23.

U.S. Pat. No. 3,562,345 to Mitsche discloses the use of molecular sieves such as mordenite catalysts in the transalkylation or disproportionation of toluene. The catalysts are characterized by a silica/alumina mole ratio from about 6 to about 12, pore openings of from about 3 to about 8 angstroms and the incorporation of catalytically active metallic materials in the oxidized or reduced state, particularly Group VIB and Group VIII metals including molybdenum, tungsten, chromium, iron, nickel, cobalt, platinum, palladium, ruthenium, rhodium, osmium, and iridium. Mitsche discloses transalkylation at temperatures from about 200° C. to about 480° C. and gives specific examples of transalkylation of toluene at temperatures of 420° C. and 450° C.

U.S. Pat. No. 3,677,973 to Mitsche et al., discloses the use of mordenite catalysts composited with an alumina salt providing a silica/alumina mole ratio of about 10 to about 30 in the transalkylation or disproportionation of toluene. The reaction conditions proposed in this patent appear similar to those set forth in the aforementioned Mitsche patent and, like the former patent, Mitsche et al., discloses incorporating Group VIB and Group VIII metals into the catalyst.

U.S. Pat. No. 4,151,120 to Marcilly discloses a process for the manufacture of a hydrocarbon conversion catalyst involving incorporating cobalt, nickel, silver or palladium in a mordenite catalyst having a silica/alumina mole ratio within the range of 10-100. After incorporation of the metal in the mordenite, the catalyst is dried and subjected to a dry calcination procedure at a temperature within the range of 300-700° C. in the presence of an inert or oxidizing gas having a moisture content of less than 1%. Marcilly discloses various examples of the dismutation of toluene under reaction conditions of 420° C., 30 bars, a space velocity (WHSV) of 5 and a hydrogen/hydrocarbon mole ratio of 5.

U.S. Pat. No. 4,723,048 to Dufresne et al. discloses a process for the dismutation of toluene employing a zeolite catalyst modified by the inclusion of metals. The catalyst is described as a sodium containing mordenite in the nature of so-called "wide pores" mordenite, i.e., mordenites who main pores have a diameter of 7-10 Angstroms or "small pores" mordenite, mordenites who main pores have a diameter of 4-6 . Angstroms. The mordenites are treated to extract sodium therefrom to provide not more than 1% by weight sodium ions and preferably not more than 0.5% by weight sodium ions. Dufresne discloses mordenites having silica/alumina ratios of 10.6 (catalyst A), 14.6 (catalyst B), 25.2 (catalyst C), and 58.6 (catalyst D) modified by the inclusion of nickel ranging from 0.43 wt. % to 2.11 wt. % and by the inclusion of nickel with certain other metals. Dufresne discloses activities of the nickel modified catalysts before and after an accelerated aging procedure at conversion rates of 10% and 45%. Catalyst C containing 1.1% nickel showed the best activity with catalyst B containing 2.11% nickel and catalyst D having 0.43% nickel showing slightly lower activities. The poorest activity was with respect to catalyst A having a nickel content of 1.81%.

SUMMARY OF THE INVENTION

In accordance with the present invention, there is provided a novel process for the disproportionation of toluene over a metal promoted molecular sieve catalyst in which catalyst activity and aging quality are enhanced for carrying out the disproportionation under relatively low temperature conditions with low incremental advance of temperature with time. In carrying out one embodiment of the invention, a mordenite disproportionation catalyst modified by the inclusion of nickel is loaded into a catalytic reaction zone. Preferably, the mordenite is an aluminum deficient mordenite, i.e., one having a silica/alumina mole ratio greater than 10 as exhibited by natural mordenite, although the invention can be carried out employing mordenite catalysts having the conventional ratio silica/alumina mole ratio of about 10. After establishing the reaction zone, a preflush gas is passed into the reaction zone at a temperature less than 300° F. This step is continued while withdrawing the gas from the reaction and progressively increasing the temperature of the reaction zone. The gas preferably is hydrogen, although other gases such as nitrogen can be employed. The toluene containing feedstock is then passed into the reaction zone.

Hydrogen is supplied concomitantly with the toluene to the reaction zone, preferably at a hydrogen/toluene mole ratio of 4 or less. At the conclusion of the initial transient conditions accompanying the initiation of toluene feed to the reaction zone, initial steady state conditions for disproportionation of toluene to benzene and xylene in the presence of the catalyst are established. The initial toluene conversion rate is at least 40% with an initial steady state reactor temperature (as measured at the reactor inlet) within the range of 600°-800° F., preferably 600° F.-700° F., and a temperature gradient across the reactor of no more than 50° F. The process is continued at a toluene conversion rate of at least 40% while retaining the activity of the catalyst, as indicated by toluene conversion, at an average progressive incremental temperature increase of no more than 7° F. per week, preferably no more than 5° F. per week as normalized by changes in space velocity of the toluene feedstock over the catalyst bed.

In a further embodiment of the invention, there is provided a toluene disproportionation process which is initiated by establishing a hydrogen environment in a catalytic reaction zone containing a mordenite disproportionation catalyst modified by the inclusion of nickel. The hydrogen environment is established at a reaction zone temperature substantially less than an intermediate temperature within the range of about 250°-500° F. The reaction zone is progressively heated, while maintaining the reaction zone under a hydrogen environment, until the intermediate temperature as described above is reached. Once the intermediate temperature range is reached, hydrogen flow through the reactor is continued for a period of several hours, normally about 4-10 hours. Thereafter, a toluene feedstock is supplied to the reaction zone along with hydrogen, preferably to provide a hydrogen/toluene mole ratio within the range of 2-4 and more preferably 3-4. After initiating the toluene feed, the reaction zone is further heated from the intermediate temperature to a higher initial toluene disproportionation temperature at which toluene conversion is at least 40%. The hydrogen/toluene mole ratio normally will be maintained relatively constant as the temperature is increased. The initial disproportionation temperature is less than 800° F. and more preferably within the range of 600°-700° F. Preferably, the reaction zone temperature, when the hydrogen environment is initiated, is no more than 150° F. and the reaction zone temperature is increased from the initial temperature to the intermediate temperature over a time period of at least 2 hours. Typically, the initial reaction zone temperature will be at ambient temperature.

BRIEF DESCRIPTION OF THE DRAWINGS

In the drawings, FIGS. 1a-1d are graphs depicting performance parameters observed in laboratory toluene disproportionation runs over three nickel modified mordenite catalysts.

FIGS. 2a and 2b are graphs depicting performance parameters associated with one of the catalysts for different hydrogen toluene mole ratios.

FIGS. 3a and 3b are graphs depicting performance parameters associated with another of the catalyst at different hydrogen/hydrocarbon mole ratios.

DETAILED DESCRIPTION OF THE INVENTION

Figure 4A:
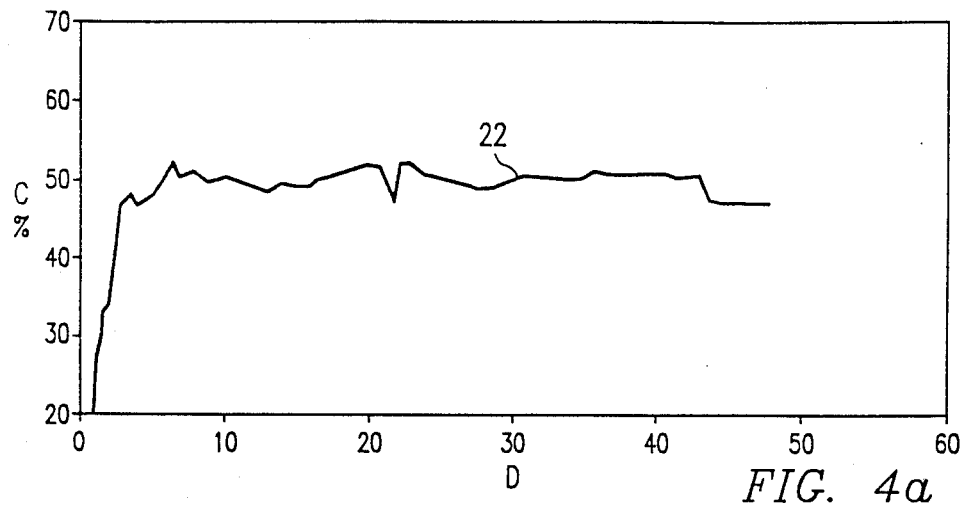
FIG. 4a, 4b and 4c are graphical presentations of performance parameters observed for a nickel modified mordenite catalyst employed in a toluene disproportionation run initiated by a conventional startup procedure.

As indicated by the patents referred to previously, the use of molecular sieve catalysts promoted with metallic based hydrogenation components based on metals from Group VIII of the Periodic Table, particularly nickel, palladium and platinum, in toluene disproportionation processes is well known in the art. In the present invention, such catalysts are used to carry out toluene disproportionation under low temperature conditions providing for relatively little loss in activity with age.

In accordance with the invention, there is provided a toluene disproportionation process employing a catalyst of the mordenite type modified by the inclusion of a metallic hydrogenation component, more specifically nickel in which catalyst activity and aging quality are enhanced to yield toluene conversion rates of at least 40%, at relatively low temperatures and low deactivation rates through the use of a low temperature startup procedure. The mordenite catalyst employed in the present invention, preferably is a moderately aluminum deficient mordenite catalyst having a silica/alumina mole ratio up to about 30 and more preferably about 20, although the invention may be carried out with naturally configured mordenite having a silica/alumina mole ratio of about 10, and it also may be carried out with the highly dealuminized mordenites such as those disclosed in the aforementioned patents to Sand, Voorhies et al., Brandenburg et al. and Butler et al. For example, aluminum deficient mordenite catalysts of the type described in the aforementioned Pat. No. 4,665,258 to Butler et al. having silica/alumina mole ratios of at least 30 may be employed. Also, the mordenite type catalysts disclosed in the aforementioned Pat. No. 4,723,048 to Dufresne et al. may be used in the invention.

The mordenite disproportionation catalyst employed in the present invention is modified by the inclusion of nickel. As indicated by the experimental data described below, best results are obtained with a nickel content of the catalyst of at least 0.8 weight percent. Low nickel contents provide toluene conversion and selectivity to xylenes and benzene but exhibit poor aging qualities. A practical upper limit in nickel content, is indicated by the experimental data to be about 1.5 wt. %. While greater amounts of nickel can be used, there appears to be no corresponding benefit from the increased nickel content.

The nickel can be incorporated into the mordenite by any suitable technique including the conventionally employed impregnation and exchange procedures described in the references referred to above. However, as indicated by the experimental data described below with respect to mordenite catalysts modified by ion exchange or by impregnation, those produced by ion exchange appeared to show better repeatability in results than those produced by impregnation.

An important feature of the present invention is a preliminary startup procedure in which the catalyst, after being loaded into the reaction zone, is brought up to an elevated temperature prior to initiating the toluene disproportionation reaction. A preflush gas, which is inert in the sense that it does not enter into reaction (1) and is suitable for establishing a nonoxidative environment in the reaction zone, is used during this initial procedure. The preflush gas may be nitrogen or hydrogen, although hydrogen is preferred. If nitrogen is used during the initial preflush step, the nitrogen circulation is replaced with hydrogen circulation and the toluene feed then started as described below.

The preflush gas procedure employed in this invention is in some respect similar to that disclosed in the aforementioned patent No. 4,665,258 to Butler et al. in that it affects a drying of the catalyst and is thus advantageous for this reason. However, whereas the Butler et al. patent contemplates passing nitrogen or hydrogen through the reaction zone at temperatures of 600°–750° F. or above, the regime involved in the present invention involves starting at a much lower temperature and then progressively increasing the temperature up to the point where the flow of toluene to the reaction zone is initiated. As described in greater detail below, in the preferred startup procedure the toluene flow is started up at a relatively low level and thereafter the toluene feed rate and the hydrogen feed rate are increased up to the operating level while further increases in temperature take place.

While the invention is not to be limited by theory, it is believed that the startup procedure of the present invention, in addition to drying the mordenite which is hygroscopic in nature, also conditions the nickel metallic hydrogenation component portion of the catalyst in a manner which ultimately results in the extremely low deactivation rates and low operating temperatures as described below. The startup procedure is believed to avoid agglomeration of the nickel in the catalyst through mechanisms in the nature of sintering reactions. The nickel, when added by an ion exchange procedure is in a nickel oxide form. By using hydrogen gas, the nickel is allowed to be reduced from the oxidized state to the metallic (zero valence) state in the course of the initial startup procedure where hydrogen is used as a preflush, or when nitrogen is initially used, upon introduction of hydrogen into the reaction zone.

Preferably, the startup procedure for the toluene disproportionation process is carried out in several stepwise phases. This procedure will be described with reference to the use of hydrogen, as is preferred, in the initial preflush step. Initially, after loading the catalyst into the reaction zone, hydrogen is passed through the reaction zone at a gas hourly space velocity (GHSV) of at least 15. During this time, the catalyst is heated from ambient temperature to an elevated temperature of at least 200° F. and preferably about 250°–350° F. over a period of several hours. During this step, the reaction zone temperature may be increased at an incremental rate of about 30°–70° F. per hour. After reaching the desired temperature, the reaction zone is retained at a temperature plateau, e.g., 300° F., for a period of at least 5 hours. Unless otherwise indicated, the reaction zone temperature referred to herein is the temperature at the reactor inlet. Depending upon the incremental temperature increase and the plateau temperature, an overall lapsed time of about 10–15 hours will occur. Thereafter, the reaction zone temperature is further increased at an incremental rate within the range of about 30°–70° F. per hour until a temperature of about 400°–500° F. is reached. Another temperature plateau can be maintained at this level, while the flow of toluene feedstock to the reaction zone is initiated. The temperature is then increased, preferably in a stepwise protocol involving one or more temperature plateaus of several hours each, while increasing the supply of hydrogen and toluene to arrive at the design rate of toluene flow for the facility. The increase here is normally less than the temperature increase occurring during the initial phase up to the time toluene flow is started. After the initial transient conditions are passed, the reaction zone will be operated at an initial disproportionation temperature within the range of about 600°–800° F., preferably 600°–700° F. to provide the requisite toluene conversion rate of at least 40%, and more preferably at least 45%.

Turning now to the drawings, FIGS. 1a–1d show the results of experimental work for catalysts described herein as catalysts A, B and C. Each of these catalysts is a nickel modified catalyst formed by incorporating nickel by ion exchange into a moderately aluminum deficient mordenite having a silica/alumina ratio of about 18. Unless otherwise indicated all of the catalysts discussed were in the form of prills of a size of about 1/16" with the mordenite associated with about 70–90% alumina as a binder.

In the experimental work depicted in FIGS. 1a–1d, catalyst A had a nickel content of 0.78 wt. %, catalyst B contained 1.39% of nickel and catalyst C contained about 1.4–1.5% nickel The deactivation rates of the catalysts are indicated in FIG. 1a in which curves 10, 12 and 14 are plots of Temperature, T, in °F., on the ordinate versus time D, in days, on the abscissa for catalysts A, B and C, respectively. In the experimental work depicted in FIGS. 1a–1d, the toluene was passed through the catalyst bed at a space velocity (WHSV) of 2 and the hydrogen to toluene mole ratio was 3:1 for catalysts A and B and 3.5:1 for catalyst C. As described below, when the hydrogen/toluene mole ratio was increased for catalysts A and B somewhat lower temperatures resulted.

In FIG. 1b, curves 10b, 12b and 14b are graphs of the weight percent toluene conversion, C, in the ordinate for catalyst A, B, C, respectively, versus time D on the abscissa. In each FIGURE, time is given in days, unless indicated otherwise. As illustrated in FIG. 1b, once the initial transient conditions were passed the toluene conversion rate for all three catalysts remain relatively constant at about 46 to 48%.

FIGS. 1c and 1d show the selectivities to benzene, and xylene, respectively, expressed as weight percent W of these components in the disproportionation product for catalysts A, B, and C. As shown by curves 10c, 12c, and 14c in FIG. 1c, and curves 10d, 12d, and 14d in FIG. 1d, benzene selectivity, after the initial transient conditions were passed, ranged from about 41 to 43 wt. %, xylene selectivity was about 45–47 wt. %. Although not shown in the experimental work, the three catalysts again, after passage of the initial transient conditions, showed very small selectivity to nonaromatics; less than about 2 wt. %. The selectivity to $C_9+$ aromatics for each of the three catalysts leveled at about 10 wt. %.

FIGS. 2 and 3 illustrate the effect of changes in the hydrogen/toluene mole ratio for catalysts A and B, respectively. FIGS. 2a and 3a are graphs of temperature, T, °F., versus time, D, in days to illustrate deactivation rates and FIGS. 2B and 3B are graphs illustrating the weight percent toluene conversion, C, on the ordinate versus time, D, in days on the abscissa.

In FIG. 2a, curves 16 and 17 show the results for hydrogen/toluene mole ratios of 3:1 and 4:1, respectively. In FIG. 2b, curves 16a and 17a show the toluene conversion rates for the respective hydrogen/toluene mole ratios of 3:1 and 4:1.

Similar information is shown in FIG. 3 for catalyst B with curves 19 and 20 in FIG. 3a and 19a and 20a in FIG. 3b indicating the results for hydrogen/toluene mole ratios of 3:1 and 4:1, respectively. As illustrated in FIGS. 2 and 3, the higher hydrogen flow rates provide for somewhat lower temperatures at roughly the same toluene conversion rates. Although not shown in the graphical presentation of experimental results, benzene and xylene selectivities were about the same for the two hydrogen/toluene ratios, once the initial startup conditions were passed.

Additional experimental work was carried out employing mordenite catalysts of varying nickel content, or in one instance, no nickel content, under different startup procedures. The nickel mordenites employed in these tests were modified by an impregnation procedure in which the catalyst was wetted with a solution of a nickel salt in an amount sufficient to fill the pores of the catalyst with the metal solution. The solvent slowly evaporated from the catalyst leaving the nickel salt in the pores. As a result, this experimental work is considered to be less representative than the experiments carried out employing ion exchange mordenite. However, as indicated by the data referred to below, the experiments do indicate gross differences between the different startup procedures.

In this experimental work, the low temperature startup procedure involved increasing the reactor containing the catalyst to a temperature of about 300° F. and holding the reactor at this temperature for 12–15 hours. Hydrogen was passed through the reactor during this stage of the operation. At the conclusion of the 12–15 period the temperature was increased at a rate of about 120° F. per hour to about 480° F. and toluene introduction was started. The temperature was increased to about 660° F. and adjusted as necessary to obtain about 43–44% toluene conversion. The space velocity (LHSV) was about 2 and the hydrogen/toluene mole ratio was about 3:1 unless stated otherwise. The runs initiated with the conventional high temperature startup procedures were carried out under similar conditions, except toluene was injected initially with hydrogen without the hydrogen preflush procedure.

Figure 4B:
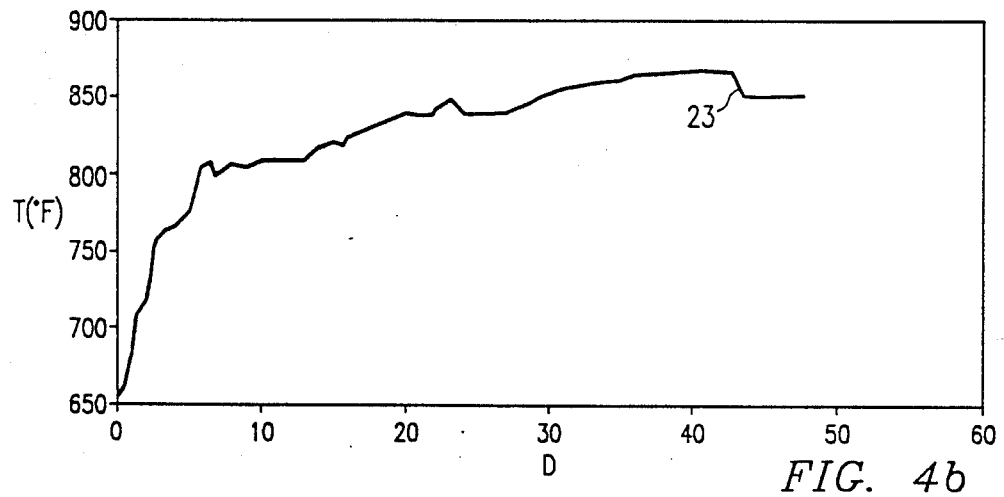
Figure 4C:
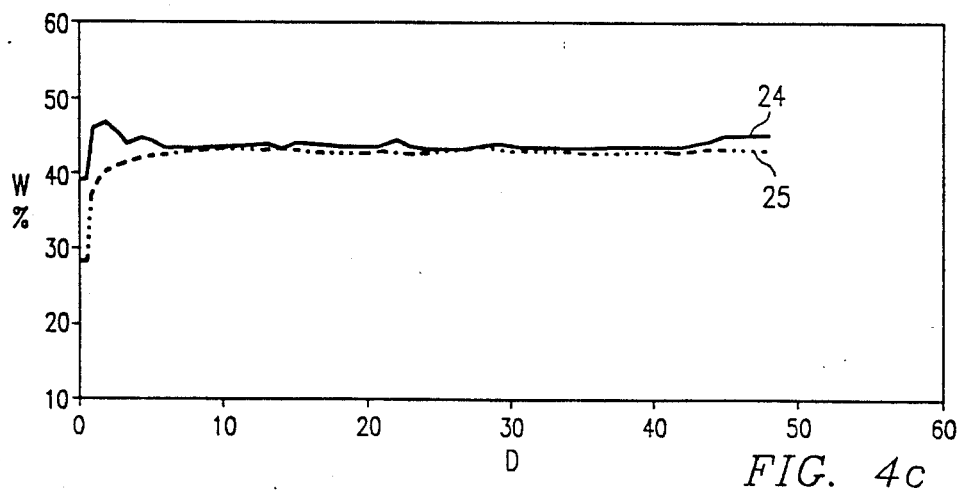

FIG. 4 illustrates the results of a toluene disproportionation run carried out over a catalyst containing 1.2% nickel employing the conventional startup procedure. FIG. 4a shows the percent toluene conversion (curve 22), FIG. 4b the reactor temperature T, °F., (curve 23) and FIG. 4c the xylene selectivity (curve 24) and benzene selectivity (curve 25), all plotted against time, D, in days. This run was carried out at a toluene conversion rate of about 50% except during the latter stages of the run when it was reduced to about 47%. The corresponding temperature was initially about 700° F. The deactivation rate, determined as the incremental increase in reactor inlet temperature required to maintain the toluene conversion rate constant was initially between 4° and 5° F. per day but decreased to about $\frac{1}{2}$° F. per day after about 4 weeks. After about 6 weeks, the temperature was decreased to about 840° F. corresponding to a toluene conversion rate of about 47%.

At the conclusion of the run illustrated in FIG. 4, the toluene and hydrogen feeds were stopped and the reactor was regenerated. The regeneration procedure involve purging the reactor with nitrogen for 2 hours, followed by increasing the reactor temperature to about 930° F. and adding a stream of air to the nitrogen feed. An exotherm was observed for about 2 hours after which the reactor temperature dropped to about 930° F. Thereafter the feed was switched to 100% air for 16 hours to complete the regeneration procedure. At the conclusion of the regeneration procedure, a second test using the conditions described previously was instituted. However, the catalyst appeared to deactivate rapidly, about 11° F. per day, and at the end of a week the run was terminated and the catalyst regenerated a second time. When a third run was reinstituted employing the regenerated catalyst, a high deactivation rate, about 9° F. per day, was again observed and the run was terminated after 1 week.

Figure 5A:
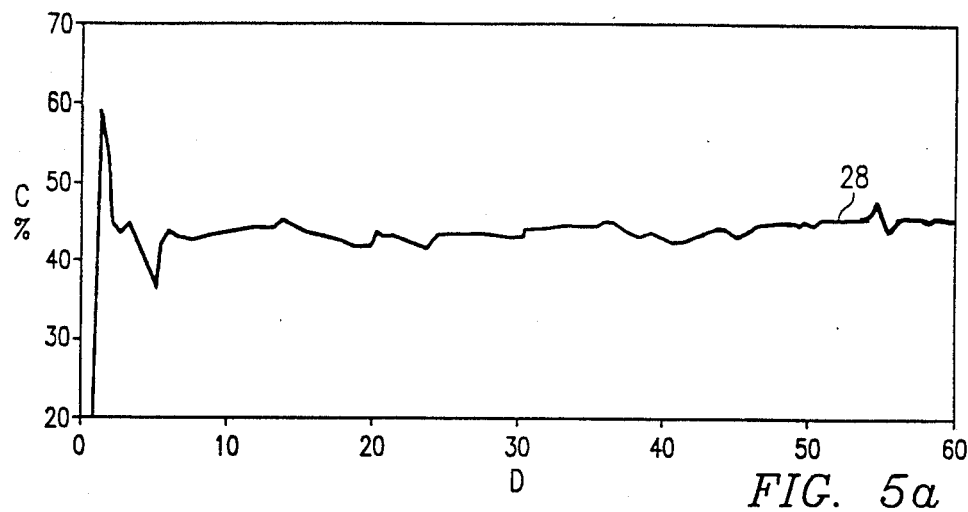
FIG. 5a, 5b and 5c are a graphical presentations of performance parameters resulting from a toluene disproportion run employing the same nickel modified catalyst but with the toluene disproportionation run initiated by a low temperature startup procedure in accordance with the present invention.
Figure 5B:
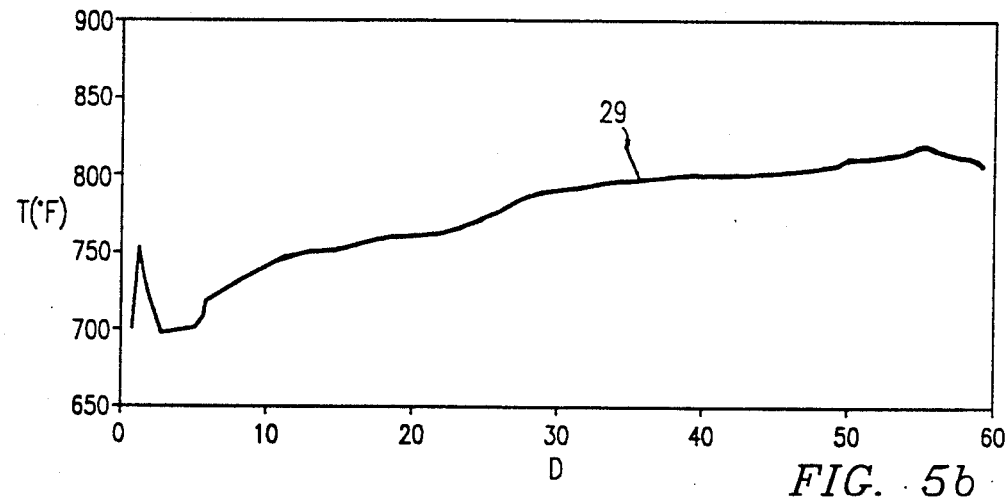
Figure 5C:
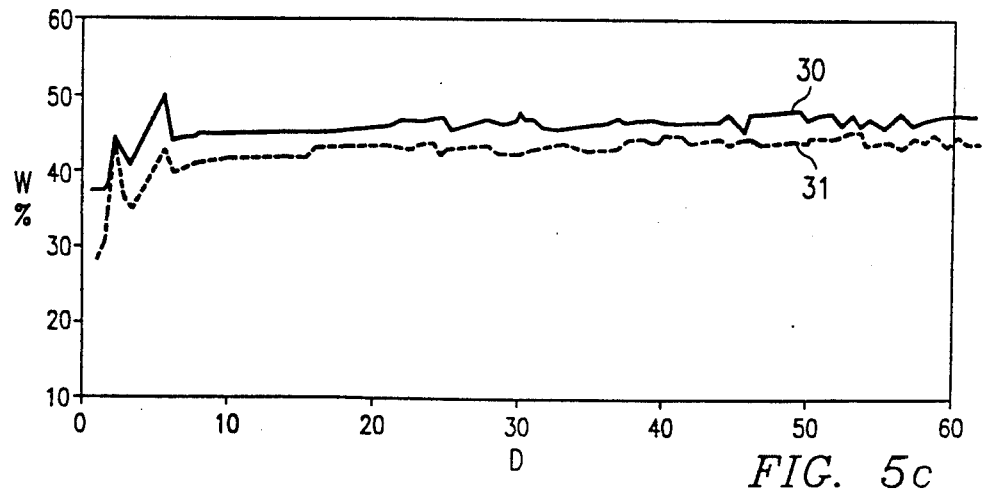

A second experimental run was carried out by using a fresh sample of the same catalyst (containing about 1.2% nickel) from the same lot as used in the experimental work depicted in FIG. 4 but with the run instituted with the low temperature procedure. Here the conversion rate was maintained at a slightly lower level of about 43 to 44%. The results of this experimental work are illustrated in FIG. 5 in which curve 28 (FIG. 5a), curve 29 (FIG. 5b), and curves 30 and 31 (FIG. 5c) are graphs of toluene conversion, reactor temperature, xylene selectivity, and benzene selectivity plotted as functions of time, D, in days. As can be seen from examination of FIG. 5, even accounting for the somewhat lower conversion rate, the reactor temperature was lower. The average deactivation rate was about 2° F. per day but when a dryer was installed to dry the feedstream (originally containing 100 ppm water), the deactivation rate dropped to less than 0.5° F. per day.

Figure 6A:
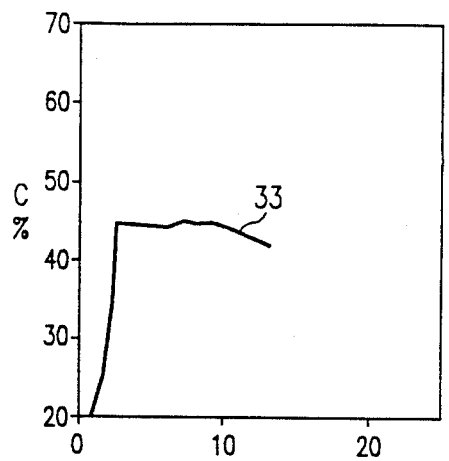
FIG. 6a, 6b and 6c are graphical presentations of performance parameters observed during a toluene disproportionation run over a mordenite catalyst free of nickel and with the run initiated by a conventional high temperature startup procedure.
Figure 6B:
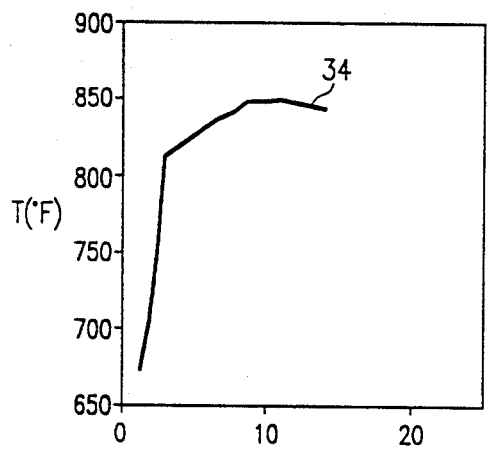
Figure 6C:
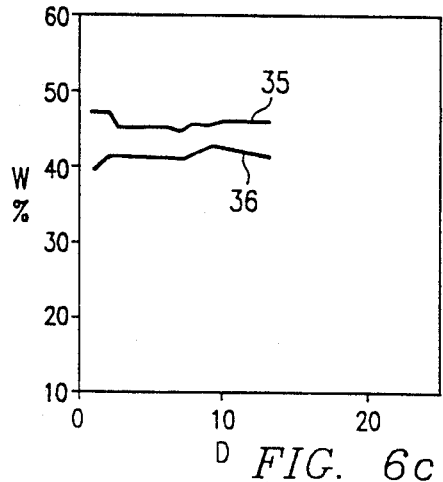

Further experimental work was carried out using a mordenite catalyst having a silica/alumina ratio of 18 as before, without nickel impregnation. The results here for this run are illustrated in FIG. 6. In FIG. 6a, curve 33 is a plot of toluene conversion and FIG. 6b curve 34 shows the reactor temperature, both plotted as a function of time. The xylene and benzene selectivity are shown by curves 35 and 36, respectively in FIG. 6c.

Figure 7A:
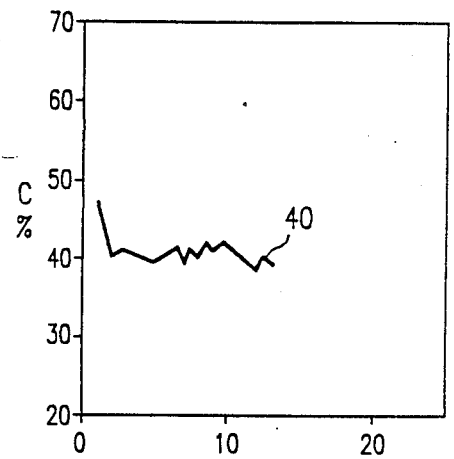
FIGS. 7a, 7b, 7c and 8a, 8b and 8c are graphical presentations of performance parameters observed during toluene disproportionation runs over catalysts from the same lot as the catalyst used in the run of FIG. 6 but modified by the inclusion of 1% nickel and employing low temperature startup procedures.
Figure 7B:
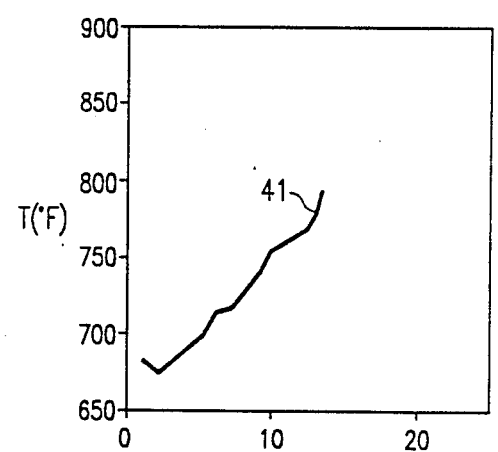
Figure 7C:
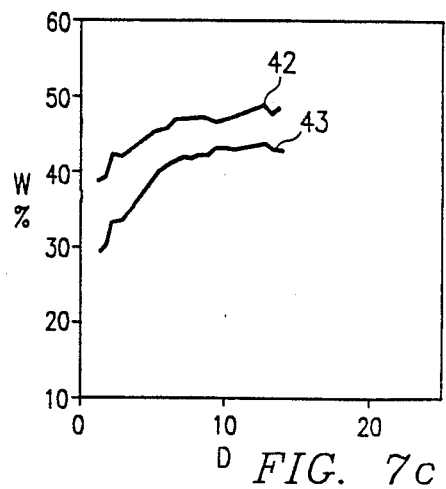
Figure 8A:
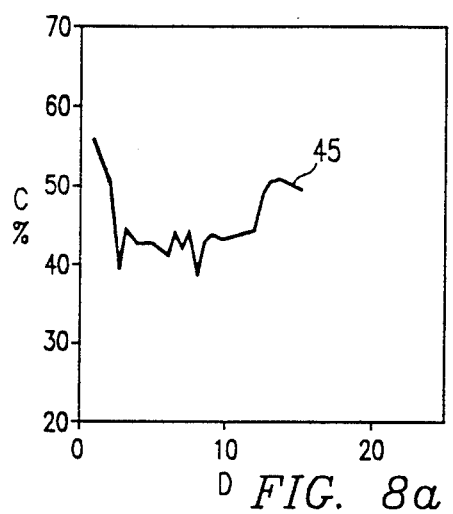
Figure 8B:
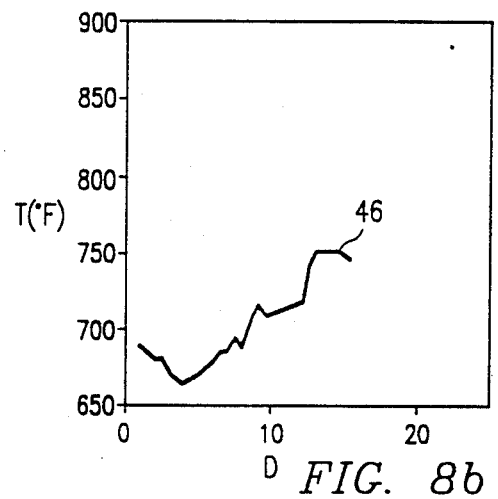
Figure 8C:
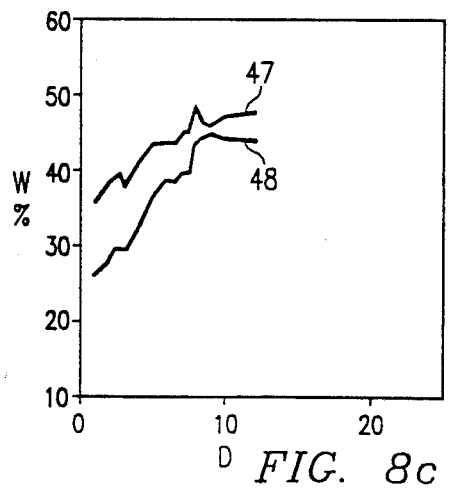

FIGS. 7 and 8 illustrate experimental work carried out with the same mordenite catalyst of FIGURE 6, but modified by the inclusion of 1% nickel by the pore filling procedure described previously. The low temperature procedure was used in both of these runs. In FIG. 7, curves 40 and 41 illustrate toluene conversion and reactor temperature respectively and curves 42 and 43 are graphs of xylene and benzene selectivities respectively. The run depicted in FIG. 7 was terminated because of the high deactivation rate and the pore selectivity to benzene.

The same catalyst was again employed in the test procedure depicted in FIG. 8. The results of this run are shown in FIG. 8 for toluene conversion (curve 45), reactor inlet temperature (curve 46) xylene selectivity (curve 47) and benzene selectivity (curve 48). The temperature here was much lower than in the previous run. The initial deactivation rate was about 5° F. per day but showed signs of declining substantially. However, the run was terminated because of the poor selectivity to benzene and the high production of $C_3$ hydrocarbons.

Additional experimental work (not shown in the drawings) was carried out using the low temperature startup procedure on mordenites containing 0.1, 0.3 and 0.6 weight percent nickel. Each of these catalysts showed high deactivation rates and high temperatures in runs which were terminated after about 2 weeks.

Figure 10A:
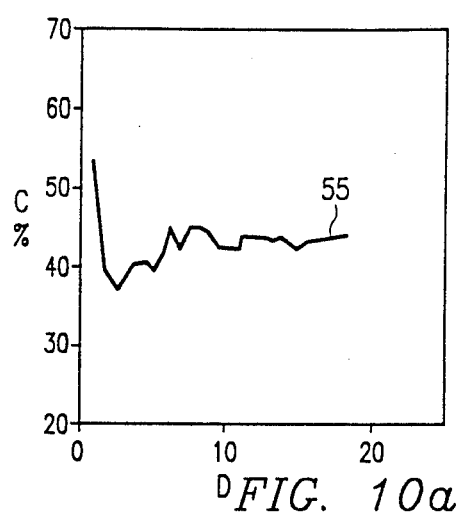
FIGS. 9a, 9b, 9c and 10a, 10b, and 10c are graphs showing performance parameters for toluene disproportion runs over different nickel modified catalysts each having a nickel content of 1.2% and with the toluene disproportion runs initiated by low temperature startup procedures.
Figure 10B:
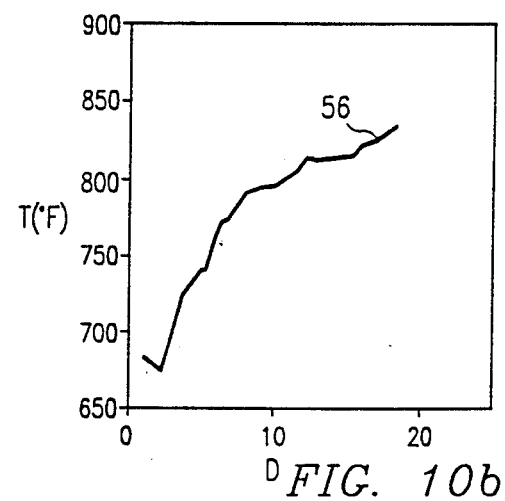
Figure 10C:
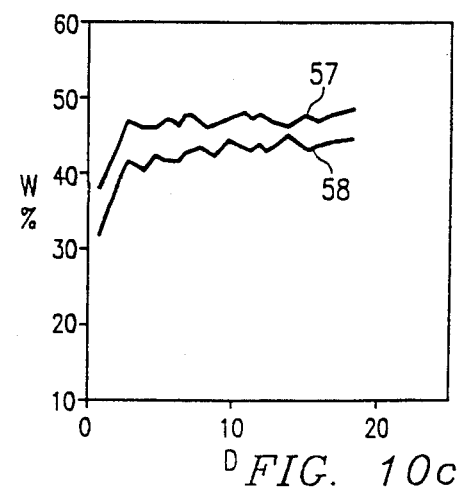
Figure 9A:
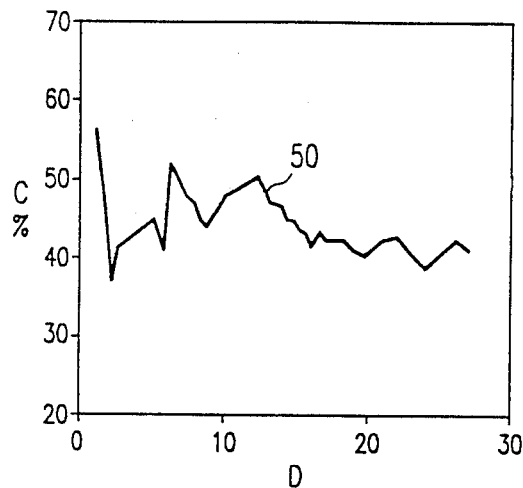
Figure 9B:
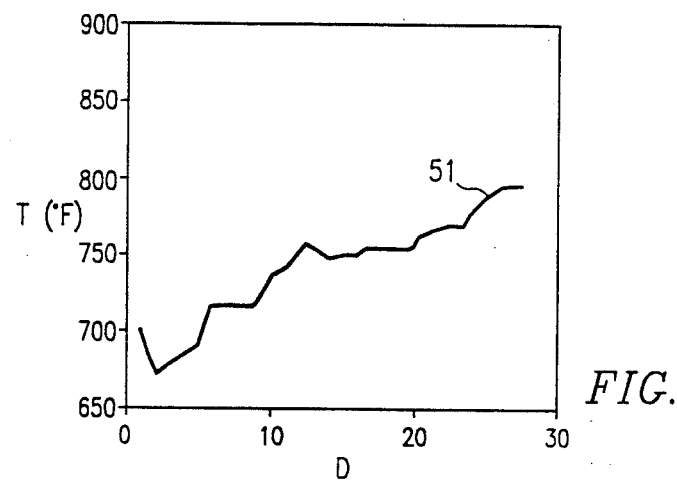
Figure 9C:
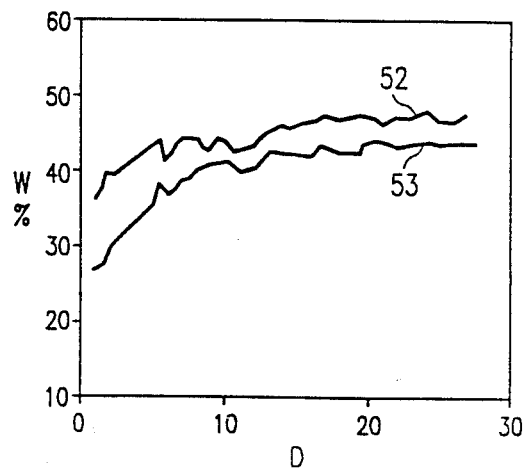

Two additional runs were carried out using two samples of fresh mordenite catalyst from different lots but each containing 1.2 weight percent nickel. The results of these tests are depicted in FIGS. 9 and 10. In FIG. 9, toluene conversion, reactor inlet temperature, xylene selectivity, and benzene selectivity are indicated by curves 50, 51, 52 and 53, respectively. In FIG. 10, toluene conversion and reactor temperatures are shown by curves 55 and 56. Xylene selectivity is shown by curve 57 and benzene selectivity by curve 58. While these runs showed low initial temperatures they were terminated because of the high deactivation rates.

As noted previously, the nickel loadings used in the experimental work depicted in FIGS. 4–10 were achieved by pore filling techniques. While good results can be obtained using this technique, as indicated by FIG. 5, the lack of reproducibility at nickel contents of 1 and 1.2 weight percent would indicate that the ion exchange technique is by far the superior mode of incorporating nickel into the mordenite catalyst.

The aforementioned patent U.S. Pat. No. 4,723,049 to Menard et al. discloses that the aging quality of an aluminum deficient mordenite catalyst, without the presence of a metallic hydrogenation component, can be enhanced by interrupting the supply of a toluene feedstock while continuing the supply of hydrogen in a so-called "hydrogen sweep". A similar mode of operation can be employed in the present invention to enhance the activity of the nickel modified mordenite catalysts as used in the present invention.

Figure 11:
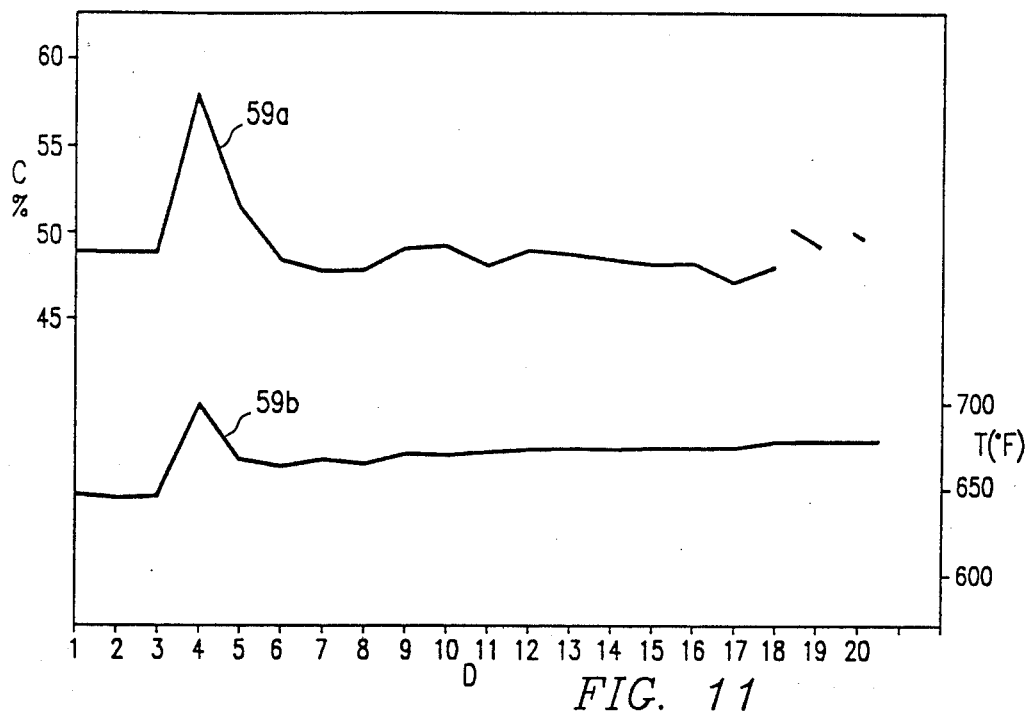
FIG. 11 is a graph showing the results of a laboratory test in which toluene flow to the reaction zone was interrupted while continuing hydrogen flow.

This mode of operation, employing the previously described catalyst C, is depicted in FIG. 11 which shows the toluene conversion and reactor temperature observed in a laboratory run extending for 19 days. In FIG. 11, curve 59 is a graph of toluene conversion C and curve 59a is a graph within that temperature T in degrees Fahrenheit plotted on the ordinate versus time D in days in the abscissa. In this experimental work, the toluene feedstock contained 150 ppm water and the hydrogen was supplied at a rate to provide a hydrogen/toluene mole ratio of 3.5:1. As illustrated in FIG. 11, the disproportionation process was conducted for 17 days with little change in condition except for a slight increase in the reactor inlet temperature. During the 18th day, the toluene feedstream was turned off for a period of 6 hours. Hydrogen flow at the previous rate continued during this time at a temperature of 675° F. The toluene feed was reinstituted and the product was sampled at 1 and 3 hours after restarting the toluene feed and showed an increase in toluene conversion as indicated by curve 59a.

During the 19th day of operation, the toluene feedstream was again shut down; this time for a period of about 16 hours, while the hydrogen sweep continued again at a temperature of about 675° F. Further samples were obtained at 1 and 3 hours after reinstituting the toluene feedstream and a further increase in toluene conversion was observed.

In providing such hydrogen sweeps during periods of feedstream shut down, the temperature of the reactor should be retained at relatively low levels consistent with the temperature during the toluene disproportionation process. Specifically, the reaction zone temperatures during the hydrogen sweep should not exceed 800° F. and normally should be in the range of 500°–800° F.

By way of further description of the invention, the nickel modified mordenite catalyst identified previously as catalyst C has been employed in a toluene disproportionation plant for a period of several months at low temperatures and low deactivation rates while achieving toluene conversion rates of about 47–48%. The toluene reactor contained about 46,000 lbs. of the catalyst in 1/16" extrudates. In the course of the startup procedure, the reactor was evacuated to about 11–12 psia to ensure that there were no leaks. It was then pressurized with nitrogen and the effluent from the reactor checked until the oxygen level in the effluent gas was less than 2 volume %. Thereafter, hydrogen was introduced into the reactor at a rate of about 35,000 standard cubic feet per hour (equivalent to a GHSV of about 33), and the reactor was pressurized. When the reactor pressure reached 50 psig, the reactor was heated to about 300° F. The incremental heating rate was about 50° F. per hour. After the reactor pressure reached a value of about 650 psig, hydrogen flow continued for about 8 hours. This resulted in drying of the catalyst and also partial reduction of the nickel from the oxidized to the zero valence state. The unit low points were then drained to ensure removal of all water from the system and the temperature was then increased to 450° F. at an incremental heating rate of 50° F. per hour.

After reaching 450° F. and holding this temperature for about one hour, toluene flow was initiated at a rate of about 5,000 barrels per day. Upon introduction of the toluene feedstream, a temperature exotherm of about 70° F. was observed across the reactor. The reactor was allowed to stabilize until the temperature rise from the inlet to the outlet of the reactor was about 50° F. The reactor temperature was then increased by about 50° F. to 500° F. The incremental heating rate here was about 15° F. per hour, substantially below that used in reaching the two previous temperature plateaus. The reactor temperature was then maintained at about 500° F. while the toluene feed rate was increased at an incremental rate of about 400 barrels per day every hour. The hydrogen feed rate was correspondingly increased to maintain the hydrogen/toluene molar ratio at about 3.5. While increasing the toluene feed rate, the temperature was maintained constant at 500° F. for about 2 hours and thereafter increased at a rate of 15° F. per hour to 550° F. When the toluene feed rate reached 9000 barrels per day (90% of design capacity), the temperature was again increased at an incremental rate of 15° F. per hour to 600° F. Thereafter, the temperature was gradually increased, and the output from the reactor monitored to arrive at a toluene conversion rate of about 47–48%.

Figure 12:
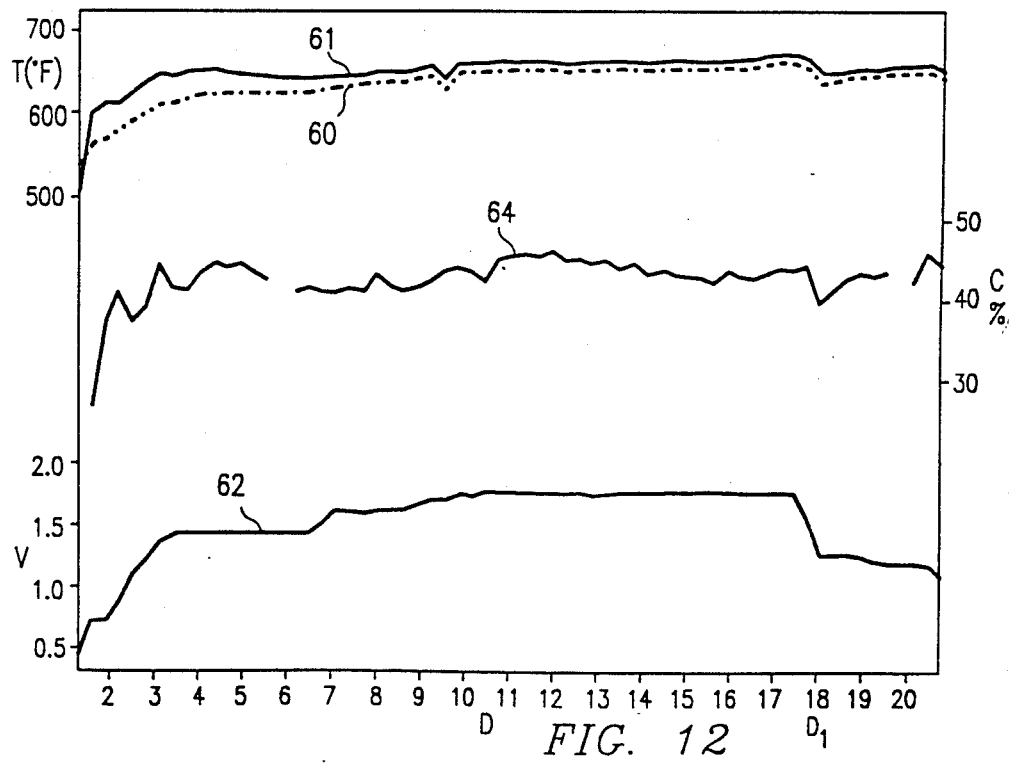
FIG. 12 is a graph presenting the results of a plant run initiated by a low temperature startup procedure in accordance with the invention and using a nickel modified mordenite catalyst for which experimental work is shown in FIGS. 1 and 2.

The results of the plant operation are depicted graphically in FIG. 12 in which a number of parameters are plotted on the ordinant versus time on the abscissa. In FIG. 12, curves 60 and 61 indicate the reactor inlet and outlet temperatures, respectively. Curve 62 is a graph of the space velocity, V, (LHSV) of the toluene feed and curve 64 is a graph of the toluene conversion rate. As can be seen from an examination of FIG. 12, the temperature gradient across the reactor was initially about 40–50° F. However, as the process approached a steady-state condition, the temperature gradient began to narrow until it reached a relatively constant value of about 10–20° F. As shown by curve 60, the deactivation rate was nearly flat and over the life of the project to date, has averaged about 3% per week or less normalized for changes in space velocity.

Normalization of the deactivation rate for changes in space velocity is indicated by the reduction in space velocity at time $D_1$ in FIG. 12. As indicated there, the space velocity was reduced from about 1.8–1.3 LSHV. This was attended by about a 30° F. reduction in inlet reactor temperature to retain about the same toluene conversion after an initial transient condition. Similarly, an increase in space velocity normally will be accompanied by an increase in temperature rate to retain a relatively constant toluene conversion rate. In order to provide normalization for variations in space velocity, the deactivation rates, as indicated by the incremental temperature advance with time, are to be determined over a relatively constant space velocity.

Having described specific embodiments of the present invention, it will be understood that modification thereof may be suggested to those skilled in the art, and it is intended to cover all such modifications as fall within the scope of the appended claims.

We claim:

1. In a method for the disproportionation of a toluene feedstock to produce a disproportionation product containing benzene and xylene, the steps comprising:
   (a) initiating a startup procedure comprising:
      (1) establishing a catalyst reaction zone by loading into said reaction zone a mordenite disproportionation catalyst modified by the inclusion of nickel into said catalyst;
      (2) establishing a hydrogen environment in said reaction zone while said reaction zone is at ambient temperature;
      (3) progressively heating said reaction zone while maintaining said reaction zone under a hydrogen environment until an intermediate temperature within the range of 250–500° F. is reached;
      (4) thereafter supplying said toluene feedstock and hydrogen to said reaction zone;
      (5) further continuing the heating of said reaction zone from said intermediate temperature to a higher initial toluene disproportionation temperature of at least 600° F.;
   (b) thereafter continuing to supply hydrogen and said hydrogen and toluene containing feedstock to said reaction zone to carry out the disproportionation of toluene to a disproportionation product containing benzene and xylene in the presence of said catalyst;
   (c) withdrawing said disproportionation product from said reaction zone.

2. The method of claim 1, wherein said ambient temperature to said intermediate temperature over a time period of at least 2 hours.

3. The method of claim 1, wherein the temperature of said reaction zone is increased from said ambient temperature to said intermediate temperature at an incremental rate within the range of 30–70° F. per hour.

4. The method of claim 3, wherein said temperature is increased at said incremental rate over a period of at least 3 hours.

5. The method of claim 1, wherein the mole ratio of hydrogen to toluene supplied to said reaction zone is maintained constant while said reaction zone temperature is increased from said intermediate temperature to said initial toluene disproportionation temperature.

6. The method of claim 1 wherein toluene and hydrogen are supplied to said reaction zone during steps (d) and (f) at rates to provide a hydrogen/toluene mole ratio within the range of 2–4.

7. The method of claim 6 wherein said hydrogen/toluene mole ratio is within the range of 3–4.

8. In a method for the disproportionation of a toluene feedstock to produce a disproportionation product containing benzene and xylene, the steps comprising:
   (a) initiating a startup procedure comprising:
      (1) establishing a catalytic reaction zone by loading into said reaction zone a mordenite disproportionation catalyst modified by the inclusion of nickel into said catalyst;
      (2) passing hydrogen into said reaction zone at an hourly rate of at least 15 GHSV;
      (3) withdrawing hydrogen from said reaction zone while continuing the passage of hydrogen into said reaction zone for a period of at least 10 hours;
      (4) during the passage of hydrogen into said reaction zone increasing the temperature and maintaining the temperature of said reaction zone within the range of 250°–500° F. for a period of at least 5 hours;
      (5) initiating the supply of toluene feedstock to said reaction zone while continuing to supply hydrogen to said reaction zone;
      (6) subsequent to the introduction of said toluene feedstock to said reaction zone, progressively increasing the rate of introducing toluene and hydrogen into said reaction zone until a desired toluene flow rate is established and thereafter continuing to supply hydrogen and toluene containing feedstock to said reaction zone to carry out the disproportionation of said toluene to a disproportionation product containing benzene and xylene in the presence of said catalyst; and
   (b) withdrawing said disproportionation product from said reaction zone.

9. The method of claim 8, further comprising the step subsequent to step (e) increasing the temperature of said reaction zone to a value sufficient, at said desired toluene flow rate, to provide a toluene conversion rate of at least 40%.

10. The method of claim of 9, wherein said temperature is within the range of 600°–800° F.

11. The method of claim 9, wherein said temperature is within the range of 600°–700° F.

12. The method of claim 10, wherein said toluene conversion rate is at least 45%.

13. The method of claim 8, wherein said mordenite disproportionation catalyst has a silica/alumina mole ratio within the range of 10–30.

14. In a method for the disproportionation of a toluene feedstock to produce a disproportionation product containing benzene and xylene, the steps comprising:
   (a) initiating a startup procedure comprising:
      (1) establishing a catalytic reaction zone by loading into said reaction zone a mordenite disproportionation catalyst modified by the inclusion of nickel onto said catalyst;
      (2) passing hydrogen into said reaction zone at a gas hourly space velocity (GHSV) of at least 15;
      (3) withdrawing hydrogen from said reaction zone while continuing the passage of hydrogen into said reaction zone at said hourly rate for a period of at least 10 hours;
      (4) during the passage of hydrogen into said reaction zone to an elevated temperature of at least 200° C. for a period of at least 5 hours;
      (5) subsequent to said period further increasing the temperature of said reaction zone by an increment of at least 100° C. and thereafter initiating the flow of toluene containing feedstock to said reaction zone while continuing the flow of hydrogen to said reaction zone;

(6) further increasing the temperature of said reaction zone by an incremental increase less than said first incremental temperature increase and maintaining said second incremental temperature increase while progressively increasing the toluene flow rate and the hydrogen flow rate into said reaction zone;

(7) thereafter further increasing the temperature of said reaction zone while further increasing the toluene flow rate to arrive at a designated toluene feed rate;

(b) thereafter continuing to supply hydrogen and toluene containing feedstock to said reaction zone to carry out the disproportionation of toluene to a disproportionation product containing benzene and xylene in the presence of said catalyst; and (c) withdrawing said disproportionation product from said reaction zone.

15. The method of claim 14, further comprising increasing the hydrogen feed rate while increasing the toluene feed rate in step (g).

16. The method of claim 14, wherein the temperature of said reaction zone is increased in step (g) to a value sufficient, at said designated toluene feed rate, to provide a toluene conversion rate of at least 40%.

17. The method of claim of 16, wherein said temperature is within the range of 600°–800° F.

18. The method of claim 17, wherein said toluene conversion rate is at least 45%.

19. The method of claim 18, wherein said temperature is within the range of 600°–700° F.

20. In a method for the disproportionation of a toluene feedstock to produce a disproportionation product containing benzene and xylene, the steps comprising:

(a) initiating a startup procedure comprising:

(1) establishing a catalytic reaction zone by loading into a reaction zone a mordenite disproportionate catalyst modified by the inclusion of nickel into said catalyst;

(2) initiating the flow of a preflush gas into said reaction zone at a temperature less than 300° F. and continuing the flow of gas into said reaction zone and withdrawing gas from said reaction zone while progressively increasing the temperature of said reaction zone;

(3) subsequent to step (2) supplying said toluene containing feedstock into said reaction zone and concomitantly with said toluene containing feedstock, supplying hydrogen to said reaction zone;

(4) thereafter establishing initial steady state conditions for the disproportionation of toluene in the presence of said catalyst to a disproportionation product containing benzene and xylene at a toluene conversion rate of at least 40%, an initial steady state reactor temperature within the range of 600–800° F. and a temperature gradient across said reactor of no more than 50° F.; and (b) continuing the supply of said toluene feedstock and hydrogen to said reaction zone to carry out the disproportionation at a conversion rate of at least 40% while retaining the activity of said catalyst as indicated by the toluene conversion rate at a progressive incremental temperature increase of no more than 7° F. per week normalized for any changes in the space velocity of said toluene feedstock over the catalyst bed.

21. The method of claim 20, wherein said toluene conversion rate is at least 45%.

22. The method of claim 20, wherein the progressive temperature increase of step (e) is no more than 5° F. per week.

23. The method of claim 20, wherein said preflush inert gas is nitrogen.

24. The method of claim 20, wherein said preflush gas is hydrogen.

25. The method of claim 20, wherein said initial steady-state temperature is within the range of 600°–700° F.

26. The method of claim 20, wherein said toluene conversion rate is at least 45%.

27. The method of claim 20, wherein said mordenite disproportionation catalyst has a silica/alumina mole ratio within the range of 10–30.

28. The method of claim 27, wherein said mordenite disproportionation catalyst has a silica/alumina mole ratio within the range of about 10–20.

29. The method of claim 20, further comprising the step of interrupting the supply of said toluene feedstock to said reaction zone and during the interruption of said toluene containing feedstock continuing to supply hydrogen to said reaction zone at a temperature of no more than 800° F. and thereafter reinstating the supply of said toluene containing feedstock to said reaction zone to reinstate said disproportionation process.

30. The method of claim 29, wherein said hydrogen is supplied during the period of interruption at a reaction zone temperature within the range of 500°–800° F.

* * * * *